United States Patent [19]
Auel et al.

[11] 3,931,294
[45] Jan. 6, 1976

[54] PRODUCTION OF 2-PHENYL-ETHYLENE PHOSPHONIC ACID

[75] Inventors: Theodor Auel, Hurth-Kendenich; Gero Heymer, Erftstadt Liblar; Hans-Werner Stephan, Cologne, all of Germany

[73] Assignee: Hoechst Aktiengesellschaft, Frankfurt, Germany

[22] Filed: June 21, 1974

[21] Appl. No.: 481,813

[30] Foreign Application Priority Data

Sept. 29, 1973 Germany............................ 2343460

[52] U.S. Cl. ........ 260/502.4 R; 260/453 P; 423/89; 423/488
[51] Int. Cl.² .......................................... C07F 9/38
[58] Field of Search.................. 260/502.4 R, 453 P

[56] References Cited
UNITED STATES PATENTS

| | | | |
|---|---|---|---|
| 2,471,472 | 5/1949 | Woodstock .................. | 260/502.4 R |
| 2,685,602 | 8/1954 | Woodstock et al. .......... | 260/502.4 R |

Primary Examiner—Joseph E. Evans
Attorney, Agent, or Firm—Connolly and Hutz

[57] ABSTRACT

Production of 2-phenyl-ethylene phosphonic acid by reacting styrene with phosphorus pentachloride in a molar ratio of about 1 : 2 in liquid phase and hydrolyzing the resulting complex 2-phenyl-ethylene phosphonic acid tetrachloride with water. The reaction is more particularly started with the use as the liquid phase of the equimolar mixture of 2-phenyl-ethylene phosphonic acid dichloride and phosphorus oxychloride obtained as an intermediary product; styrene and phosphorus pentachloride are introduced thereinto with continuous agitation; resulting complex 2-phenyl-ethylene phosphonic acid tetrachloride is partially hydrolyzed by adding a predetermined quantity of water to an equimolar mixture of 2-phenyl-ethylene phosphonic acid dichloride and phosphorus oxychloride; a portion of the resulting clear solution is continuously used as the liquid phase and phosphorus oxychloride is continuously distilled off under reduced pressure from the balance portion of the solution; remaining 2-phenyl-ethylene phosphonic acid dichloride is hydrolyzed by continuous addition of overstoichiometric proportions of water to an aqueous solution of 2-phenyl-ethylene phosphonic acid; the aqueous solution is cooled and crystalline phosphonic acid is precipitated therefrom.

3 Claims, No Drawings

PRODUCTION OF 2-PHENYL-ETHYLENE PHOSPHONIC ACID

The present invention relates to a continuous process for making 2-phenyl-ethylene phosphonic acid of the formula $$C_6H_5-CH=CH-P(O)(OH)_2$$

which is an accumulator acid suitable for use in the commercial concentration of tinstone by flotation.

It is known that styrene can be reacted with phosphorus pentachloride in the presence of an inert solvent so as to obtain an intermediary addition product, which can be dehydrochlorinated with the resultant formation of 2-phenyl-ethylene phosphonic acid tetrachloride in complex combination with phosphorus pentachloride. By subjecting the complex phosphonic acid tetrachloride to hydrolysis, it is possible to produce free 2-phenyl-ethylene phosphonic acid via the stage of phosphonic acid dichloride. The entire reaction is illustrated by the following scheme of formulae:

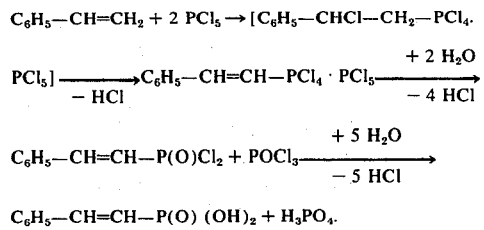

In view of the fact that the reaction of styrene with phosphorus pentachloride is an exothermal liquid matter/solid matter reaction, wherein a solid product (adduct of 2-phenyl-ethylene phosphonic acid tetrachloride and phosphorus pentachloride) is obtained again in the first reaction stage, it is possible for the reaction to be effected in the presence of a solvent or dispersing agent, for reasons of improved heat transmission. As described in the literature, it is good practice to use a hydrocarbon or chlorinated hydrocarbon for that purpose.

The above reaction has been described by E. Bergmann and A. Bondi [Ber. 63, 1158 – 1173 (1930)]. More particularly, styrene has been reacted with phosphorus pentachloride in the molar ratio of 2 : 1 in the presence of benzene as a dispersing agent with the resultant formation of an addition compound. After hydrolysis, crude 2-phenyl-ethylene phosphonic acid is obtained in a yield of about 59 %, based on styrene. Recrystallization from dibromo-ethane produces the pure acid in a total yield of 34 %.

As taught by G. M. Kosolapoff and W. F. Huber [J. Am. Chem. Soc. 68, 2540–41 (1946)] it is possible to produce 2-phenyl-ethylene phosphonic acid without the direct use of phosphorus pentachloride as a starting material. To this end, it is necessary to introduce chlorine into a blend of styrene and phosphorus trichloride (molar ratio 1 : 1) which is diluted with about five times its volume of benzene. The reaction mixture so obtained is hydrolyzed and desirable phosphonic acid is obtained in a yield of about 36 %. In this reaction, a considerable proportion of the styrene used goes into chlorination products and does not participate in the reaction to phosphonic acid. More particularly, the chlorination of phosphorus trichloride occurs parallel with the chlorination of styrene and substantially 1,2-dichloro-1-phenyl-ethane is produced.

A further process for making 2-phenyl-ethylene phosphonic acid has been described in DL-PS 76 974, wherein phosphorus trichloride is chlorinated in the presence of an inert solvent, e.g. carbon tetrachloride, to give phosphorus pentachloride. This latter product is not isolated but reacted with styrene. Following this, the reaction product is partially hydrolyzed, solvent and by-products are separated in a manner not specifically described, and the product is completely hydrolyzed to phosphonic acid. The yield in which phosphonic acid is obtained is not indicated.

One feature which is common to all those processes which have been referred to hereinabove resides in the fact that they are carried out intermittently and that solvents are used therein. The re-use of the solvents is a problematic procedure as they are partially strongly contaminated and are required to be purified by costly methods.

The manufacture of 2-phenyl-ethylene phosphonic acid by chlorinating a blend of styrene and phosphorus trichloride and hydrolyzing the chlorinated product is handicapped by the formation of considerable quantities of 1,2-dichloro-1-phenyl-ethane which is not acceptable in effluent water. It is difficultly biodegradable and rather toxic for microbes.

The chlorination of phosphorus trichloride in carbon tetrachloride, described in DL-PS 76 974, is difficult to carry out under commercial conditions, under which the chlorine feed inlet is very likely to become clogged by phosphorus pentachloride which crystallizes out. In addition, towards the end of the chlorination, the solution tends to precipitate compact phosphorus pentachloride, which is rather inactive with respect to its further reaction with styrene. After partial hydrolysis to the phosphonic acid dichloride stage, the solvent and by-products, which substantially consist of carbon tetrachloride and phosphorus oxychloride, are separated. The distillative separation of this mixture into its pure components calls for the use of considerable technical expenditure, for example, distillation columns provided with an extremely high number of trays.

In summary, all the processes described heretofore for making 2-phenyl-ethylene phosphonic acid are commercially unattractive procedures for the following reasons:

a. They are carried out intermittently.
b. The yields of phosphonic acid, inasmuch as they have been identified, are rather low.
c. The reactions are required to be carried out in the presence of solvents, which can generally not be used again.
d. The reactions partially produce toxic by-products which are difficultly degradable and must be disposed of by subjecting them to specific treatment (e.g. incineration), whereby the processes are rendered even more costly.

The present invention now provides a process for the continuous manufacture of 2-phenyl-ethylene phosphonic acid which is obtained in high yields and purity.

In accordance with the present invention, the process is effected in the absence of any supplementary solvent or dispersing agent. In other words, the present process compares very favorably with the prior art methods, in respect of its economy.

The process of the present invention can, for example, be effected in the following manner: A solution preferably of an equimolar blend of 2-phenyl-ethylene phosphonic acid dichloride and phosphorus oxychloride is admixed, with agitation, with a certain amount of phosphorus pentachloride, which is partially dissolved and of which the bulk is kept in suspension. The resulting mixture is reacted with a suitable quantity of styrene and the resulting addition compound is partially hydrolyzed to 2-phenyl-ethylene phosphonic acid dichloride and phosphorus oxychloride, by the addition of stoichiometric proportions of water. The fraction of these two products originating from the reaction is separated from the solution and delivered to a collecting tank, before it is further processed. The residual solution is used once again for reaction of phosphorus pentachloride and styrene therein, in the manner described. Following the addition of the necessary quantity of water, a proportionate share of hydrolyzate is taken from the reactor.

This procedure is repeated as often as desirable.

The present invention thus provides a process, wherein phosphorus pentachloride is reacted with styrene in the secondary products originating from the partial hydrolysis, as solvents or dispersing agents. As has unexpectedly been found, neither 2-phenyl-ethylene phosphonic acid dichloride nor phosphorus oxychloride do react with, or homopolymerize, styrene, under these conditions. It has also unexpectedly been found that the addition of stoechiometric proportions of water to the reaction mixture effects hydrolysis exclusively of the complex 2-phenyl-ethylene phosphonic acid tetrachloride, whereas the 2-phenyl-ethylene phosphonic acid dichloride and phosphorus oxychloride, respectively, which per se are hydrolyzable, remain unchanged.

In order to react phosphorus pentachloride with styrene substantially quantitatively within relatively short reaction periods, it is necessary for the suspension of phosphorus pentachloride or the resulting 2-phenyl-ethylene phosphonic acid dichloride to remain stirrable in the reaction medium, during the reaction. Failing this, a considerable proportion of the phosphorus pentachloride used becomes embedded in reaction product, whereby it is substantially or even completely withdrawn from further reaction with styrene. The suspensions remain stirrable provided that reaction medium and resulting hydrolyzate are used in a ratio by volume of at least 2 : 1, following partial hydrolysis.

The reaction of phosphorus pentachloride with styrene in accordance with the present invention should preferably be effected with the use of a "dispersing aid" as the reaction medium, in the initial reaction stage. The useful dispersing aids include more particularly organic solvents, such as aliphatic or aromatic hydrocarbons, e.g. petroleum ether, benzene, toluene or xylene, halogenated hydrocarbons, e.g. carbon tetrachloride, dichloroethane, dibromoethane, di-, tri- or tetrachloroethylene, or phosphorus oxychloride, this latter being preferably used.

Experiments have shown that the reaction system is free from the "dispersing aid" after a relatively minor number of passages. In those cases in which the process of the present invention is effected in such a manner that the increase in volume originating from the reaction is 50 % of the starting volume and that the surplus volume is removed in each particular case after partial hydrolysis, it is found that the "dispersing aid" used is removed substantially quantitatively from the reaction system, after altogether 20 passages. Needless to say the most advantageous "dispersing aid" is phosphorus oxychloride (this being a secondary compound originating from the reaction itself and thus no foreign byproduct). If use is made thereof, the liquid reaction medium contains a predominant proportion thereof in the initial reaction stage. However, after as little as 20 passages, the reaction medium is comprised of an equimolar mixture of phosphorus oxychloride and 2-phenyl-ethylene phosphonic acid dichloride.

The partial hydrolyzate, which is an intermediary product and which substantially consists of 2-phenyl-ethylene phosphonic acid dichloride and phosphorus oxychloride, is freed from phosphorus oxychloride by distillation. The distillation should preferably be carried out continuously under vacuum, e.g., under pressures within the range 65 and 200 mm of mercury, more preferably 100 mm of mercury, by delivering the mixture to be separated into its components to a heated distillation column. The jacket of the distillation column may be heated to tempera-tures within the range 55 and 110°C, preferably 75°C. 98 % of the distillate so produced is phosphorus oxychloride, which can be reused as "dispersing aid," or for further reactions. The column base product is 2-phenyl-ethylene phosphonic acid dichloride containing a minor residual quantity of phosphorus oxychloride.

The crude 2-phenyl-ethylene phosphonic acid dichloride is then hydrolyzed to 2-phenyl-ethylene phosphonic acid, preferably with the use of a suitable column which is fed with metered quantities of dichloride and simultaneously with four to seven times the quantity by weight of water. The mixture to be hydrolyzed assumes a temperatures of about 60°C.

The effluent matter coming from the column, containing dissolved 2-phenyl-ethylene phosphonic acid, is delivered to two parallel alternately actuated agitator vessels, in which the phosphonic acid crystallizes out almost quantitatively, after cooling to room temperature. The resulting 2-phenyl-ethylene phosphonic acid is separated from its aqueous phase by filtration, preferably by continuous centrifugation.

Hydrogen chloride which originates from the two hydrolyzing operations can be reco-vered continuously as a 30 % HCl by-product, by means of an absorption column.

The present invention relates more particularly to a process for making 2-phenyl-ethylene phosphonic acid by reacting styrene with phosphorus pentachloride in a molar ratio of about 1 : 2 in liquid phase and hydrolyzing the resulting complex 2-phenyl-ethylene phosphonic acid tetrachloride with water, which comprises starting the reaction with the use, as the liquid phase, of the equimolar mixture of 2-phenyl-ethylene phosphonic acid dichloride and phosphorus oxychloride obtained as an intermediary product; introducing styrene and phosphorus pentachloride thereinto with continuous agitation; partially hydrolyzing the complex 2-phenyl-ethylene phosphonic acid tetrachloride by adding a predetermined quantity of water to an equimolar mixture of 2-phenyl-ethylene phosphonic acid dichloride and phosphorus oxychloride; continuously using as the liquid phase a portion of the resulting clear solution and continuously distilling off under reduced pressure phosphorus oxychloride from the balance portion of the solution; hydrolyzing remaining 2-phenyl-ethylene phosphonic acid dichloride by continuous addition of overstoichiometric proportions of water to an aqueous solution of 2-phenyl-ethylene phosphonic acid; cooling the aqueous solution and effecting the precipitation of crystalline phosphonic acid therefrom.

In accordance with a preferred feature of the present process, the liquid starting phase comprised of an equimolar mixture of 2-phenyl-ethylene phosphonic acid dichloride and phosphorus oxychloride is prepared by stepwise operation comprising using once as the initial liquid phase an inert solvent, which is selected from hydrocarbons and halogenated hydrocarbons, preferably phosphorus oxychloride; introducing styrene and phosphorus pentachloride thereinto; hydrolyzing the resulting mixture by means of water; continuously using a portion of the resulting solution as liquid starting phase; and recover-ing 2-phenyl-ethylene phosphonic acid from the solution balance portion.

The reactions in the process of the present invention can be carried out at temperatures within the range 0° and 90°C, preferably within the range 20° and 70°C.

In accordance with the present invention, it has also been found advantageous to use the liquid phase an at least two-third portion of the intermediary product mixture comprised of 2-phenyl-ethylene phosphonic acid dichloride and phosphorus oxychloride, and to subject an at most one-third portion thereof to further reaction to 2-phenyl-ethylene phosphonic acid. It is possible for the 2-phenyl-ethylene phosphonic acid dichloride to be hydrolyzed with four to seven times its quantity of water. The partial hydrolysis of complex 2-phenyl-ethylene phosphonic acid tetrachloride and the hydrolysis of 2-phenyl-ethylene phosphonic dichloride give rise to the evolution of hydrogen chloride, which should preferably be absorbed in water and recovered in the form of hydrochloric acid, for further use thereof.

EXAMPLE 500 cc of phosphorus oxychloride (liquid phase) was placed in a reactor having a capacity of 2 liters and 520 g (2.5 mols) of phosphorus pentachloride was introduced thereinto with agitation and exclusion of moisture. A suspension was obtained and 130 g (1.25 mols) of styrene was metered thereinto within 15 minutes, whereby the temperature of the reaction mixture increased from 24° to 48°C. The whole was allowed to further react for 15 minutes at that temperature. The resulting complex 2-phenyl-ethylene phosphonic acid tetrachloride, which was a stirrable suspension, was partially hydrolyzed to 2-phenyl-ethylene phosphonic acid dichloride and phosphorus oxychloride by dropwise addition, within 10 minutes, of 45 g (2.5 mols) of water to the reaction mixture, whereby the temperature increased to 56°C. Once the water was added, a clear solution was obtained which had a total volume of 750 cc and of which a 250 cc portion was continuously delivered to an intermediate container. The remaining solution (500 cc liquid phase) was used again for the reaction of phosphorus pentachloride and styrene therein and hydrolysis. A proportionate share of liquid was removed and the procedure repeated as often as desirable. The partial hydrolyzate (250 cc) was taken from the intermediate container and continuously injected into a distillation column heated to 75°C, which was operated under a pressure of 100 mm of mercury. Phosphorus oxychloride which went over was condensed with the use of an efficient cooler and recovered as a by-product, in a receiver. Crude 2-phenyl-ethylene phosphonic acid dichloride was obtained as the base product which was continuously pumped, while hot, into a hydrolysis column which was simultaneously fed with 5 times the quantity of water. The aqueous phosphonic acid solution which left the column at a temperature of about 60°C was delivered to two parallel, alternately actuated crystallizers, in which 2-phenyl-ethylene phosphonic acid was all-owed to crystallize out, while cooling and with agitation. The product was continuously separated in a centrifuge. Hydrogen chloride gas evolved during the individual reaction stages, was passed through an absorption column and recovered as a further by-product, in the form of 30 % hydrochlorid acid. 192 g of 2-phenyl-ethylene phosphonic acid (84 % of the theoretical yield, based on styrene) was obtained per passage, in the form of a white crystalline means melting within the range 142° and 145°C. After further recrystallization from hot water, it melted within the range 154° and 155°C.

We claim:

1. In a process for making 2-phenyl-ethylene phosphonic acid by reacting with styrene with phosphorus pentachloride in a molar ratio of about 1 : 2 in liquid phase and hydrolyzing the resulting complex 2-phenyl-ethylene phosphonic acid tetrachloride with water, the improvement which comprises starting the reaction with the use, as the liquid phase (A), of the equimolar mixture of 2-phenyl-ethylene phosphonic acid dichloride and phosphorus oxychloride obtained as an intermediary product; introducing styrene and phosphorus pentachloride thereinto with continuous agitation; partially hydrolyzing the complex 2-phenyl-ethylene phosphonic acid tetrachloride by adding a predetermined quantity of water to obtain an equimolar mixture of 2-phenyl-ethylene phosphonic acid dichloride and phosphorus oxychloride; continuously using as the liquid phase (A) at least two thirds of the resulting clear solution and continuously distilling off under reduced pressure phosphorus oxychloride from the remainder of the solution; hydrolyzing the remaining 2-phenyl-ethylene phosphonic acid dichloride by admixing it with an overstoichiometric proportion of water to obtain an aqueous solution of 2-phenyl-ethylene phosphonic acid; cooling the aqueous solution and effecting the precipitation of crystalline phosphonic acid therefrom.

2. The process as claimed in claim 1, wherein the reactions are effected at temperatures within the range 0° and 90°C.

3. A process as claimed in claim 1, wherein 2-phenyl-ethylene phosphonic acid dichloride is hydrolyzed with the use of four to seven times its quantity by weight of water.

* * * * *

UNITED STATES PATENT AND TRADEMARK OFFICE
CERTIFICATE OF CORRECTION

PATENT NO. : 3,931,294
DATED : JANUARY 6, 1976
INVENTOR(S) : THEODOR AUEL ET AL

It is certified that error appears in the above-identified patent and that said Letters Patent are hereby corrected as shown below:

On the cover sheet, first column, under "Foreign Application Priority Data" change "Sept. 29, 1973" to --August 29, 1973--.

Column 4 line 33 change "temperatures" to --temperature--.

Column 6 line 23 change "means" to --mass--.

Column 6 line 28 delete "with" (first occurence).

Signed and Sealed this eighth Day of June 1976

[SEAL]

Attest:

RUTH C. MASON
*Attesting Officer*

C. MARSHALL DANN
*Commissioner of Patents and Trademarks*